United States Patent
Chalker et al.

(10) Patent No.: US 6,770,462 B1
(45) Date of Patent: Aug. 3, 2004

(54) METHODS FOR PRODUCING MODIFIED NUCLEIC ACID MOLECULES

(75) Inventors: Alison F. Chalker, Trappe, PA (US); David J. Holmes, West Chester, PA (US); Robert Dwayne Lunsford, Pottstown, PA (US); James Yigong Ge, South San Francisco, CA (US)

(73) Assignees: SmithKline Beecham Corporation, Philadelphia, PA (US); SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/009,315

(22) PCT Filed: May 4, 2000

(86) PCT No.: PCT/US00/12103
§ 371 (c)(1),
(2), (4) Date: Nov. 5, 2001

(87) PCT Pub. No.: WO00/68428
PCT Pub. Date: Nov. 16, 2000

Related U.S. Application Data

(60) Provisional application No. 60/133,391, filed on May 10, 1999.

(51) Int. Cl.[7] ............................................... C12P 19/34
(52) U.S. Cl. ..................................... 435/91.5; 435/91.2
(58) Field of Search ................................ 435/91.2, 91.5

(56) References Cited

PUBLICATIONS

Wach, A, PCR–synthesis of marker cassettes with long flanking homology regions for gene disruptions in *S. cerevisiae*. Yeast 12(3):259–265 (Mar. 1996).*

Claverys, J–P et al. Construction and evaluation of new drug–resistance cassettes for gene disruption mutagenesis in *Streptococcus pneumonaie*, using an ami test platform. Gene 164(1):123–128 (Oct. 1995).*

Brush, M. Up on blocks: a profile of thermal cyclers with interchangeable blocks. The Scientist 12(20):21 (Oct. 1998).*

Zhong, D. et al. A PCR–based method for site–specific domain replacement that does not require restriction recognition sequences. BioTechniques 15(5):874, 876–878 (1993).*

Nikawa, et al., "PCR– and ligation–mediated synthesis of marker cassettes with long flanking homology regions for gene disruption in *Saccharomyces cerevisiae*", Nucleic Acids Research, 26(3):860–861 (1998).

* cited by examiner

*Primary Examiner*—Diana B. Johannsen
(74) *Attorney, Agent, or Firm*—Jason C. Fedon; Edward R. Gimmi; Charles M. Kinzig

(57) ABSTRACT

A method for inserting a cassette into a nucleic acid molecule to produce a modified nucleic acid molecule, e.g., a nucleic acid-cassette fusion, is described. The method involves the use of polymerase chain reaction, thereby permitting precise targeting of the desired site in the molecule, but does not require ligation. Also described is the use of this method for high throughput screening the resulting modified nucleic acid molecules.

2 Claims, No Drawings

METHODS FOR PRODUCING MODIFIED NUCLEIC ACID MOLECULES

This is a 371 of International Application No. PCT/US00/12103, filed 04 May 2000, which claims benefit from the following Provisional Application No. 60/133,391, filed 10 May 1999.

FIELD OF THE INVENTION

The invention relates generally to methods for generating modified nucleic acid molecules, and more particularly, to the use of polymerase chain reaction to generate gene knockouts and nucleic acid fusion molecules.

BACKGROUND OF THE INVENTION

There are a variety of reasons which make the modification of nucleic acid sequences, particularly genes, desirable. The classical strategy for gene disruption requires the isolation of a gene and digestion with restriction enzymes [R. Rothstein, *Methods Enzymol.*, 101:202–211 (1983)]. However, the use of restriction enzymes to digest the DNA fragments sometimes makes it difficult to construct appropriate fragments disrupted by a marker DNA. To overcome this problem, several methods utilizing polymerase chain reaction (PCR) for constructing such deletions have been developed. However, it is still necessary to isolate the DNA fragment of interest, or to use a variety of complex steps [D. C Amberg et al, *Yeast*, 11:1275–1280 (1995); A. Wach etal, *Yeast*, 10:1793–1808 (1994); A. Wach, *Yeast*, 12:259–265 (1996)].

One recently described method describes a strategy for constructing gene disruption cassettes by means of PCR and ligation. See, J. Nikawa and M. Kawabat, *Nucleic Acids Res.*, 26(3):860–861 (1998). In a first step, two separate regions of a target gene are PCR amplified with primers specific for the target sequence and genornic DNA as a template. Secondly, the two PCR products are ligated with a DNA fragment of a marker gene through two separate reactions. The ligated fragments are then PCR amplified separately. Following amplification the PCR amplified fragments are mixed, denatured, annealed, and extended with DNA polymerase. Finally, the product is PCR amplified with the outermost primers.

Despite these recent advances, there remains a need for methods for modifying nucleic acid molecules which are more efficient, yet permit precise engineering at the target site.

SUMMARY OF THE INVENTION

The method of the invention provides a simple method for precisely generating a modified nucleic acid molecule to contain a deletion and/or an insertion. Advantageously, this method does not require ligation and is well suited for use in automated formats, including high throughput formats.

In one aspect the invention provides a three-stage method for inserting a cassette into a nucleic acid molecule to produce a modified nucleic acid molecule fusion without requiring ligation. In the first stage, the method involves amplifying two separate regions of a selected nucleic acid molecule and a cassette. The two regions of the nucleic acid molecule have nucleotide sequences flanking a site in the molecule targeted for disruption, whereby the amplification produces a first amplification product of nucleotide sequences upstream of the target site and a second amplification product of nucleotide sequences downstream of the target site. The cassette has sequences at its 5' and 3' ends which overlap with sequences of the two regions of the nucleic acid molecule. In the second stage, the amplified cassette product is mixed separately with the first or second amplification products resulting from amplification of the nucleic acid molecule. The cassette and first amplification product are amplified by PCR, thereby forming a first fusion product consisting of the first amplification product fused to the 5' end of the first strand of the cassette. The cassette is also mixed with the second amplification product and this mixture is amplified to form a second fusion product consisting of the second amplification product fused to the 3' end of the first strand of the cassette. In a third stage, the first and second fusion products are mixed and amplified by PCR, thereby producing a modified nucleic acid molecule comprising the cassette in the target site of the selected nucleic acid molecule. Desirably, the resulting modified nucleic acid molecule is amplified via polymerase chain reaction.

In another aspect, the invention provides a novel method for performing amplifying selected sequences by PCR, which is particularly well suited for use in the stage three of the method of the invention. In this method, a mixture containing the fusion products prepared according to stage 2 of the method of the invention is heated for about 5 minutes in the absence of polymerase or primers at about 94° C., cooled to 50° C. over about 30 minutes, at which temperature it is maintained for about 5 minutes or longer. A thermostable polymerase is then added to the mixture, which is heated to about 72° C. for about 5 minutes, and mixed with a forward primer P1 for the first region and a reverse primer P4 for the second region. The resulting mixture is then amplified using PCR to produce a modified nucleic acid molecule comprising the first and second regions of the nucleic acid sequence flanking the cassette.

In a further aspect, the invention provides a two stage method of producing a modified nucleic acid moleucle without ligation. The method involves producing two separate regions of a nucleic acid molecule and a cassette as in stage I of the three stage method of the invention. Thereafter, the three products are mixed and subjected to amplification by PCR, as described in the aspect above. Thus, this embodiment of the invention permits elimination of stage 2 of the three-stage method.

In yet a further aspect, the invention provides modified nucleic acid sequences produced using the method of the invention.

In yet another aspect, the present invention provides a method of high throughput preparation of disrupted Streptococcus DNA sequences without ligation. This method involves mixing (a) a nucleic acid molecule comprising Streptococcus DNA sequences comprising a first region upstream of a site in the Streptococcus DNA targeted for disruption and a second region downstream of the target site, said first and second region each having a first and second end, (b) a cassette comprising at one end, nucleotide sequences which overlap with nucleotides at the second end of the first region, and at its other end, nucleotides which overlap with nucleotides of the first end of the second region, and (c) primers for the first and second regions in each of the wells of a plate containing a plurality of reaction wells. This mixture is then subjected to PCR, thereby amplifying the first and second regions of the selected Streptococcus DNA sequences. The cassette and the amplified first and second regions of the Streptococcus DNA sequences are then mixed and subjected to polymerase chain reaction to produce a nucleic acid fusion molecule comprising the first and second regions of the Streptococcus DNA sequence flanking the cassette.

Other aspects and advantages of the invention will be readily apparent from the detailed description of the invention.

DETAILED DESCRIPTION OF THE INVENTION

The present invention provides a novel method for rapidly generating modified nucleic acid molecules, wherein the modification involves insertion of a cassette and/or deletion of desired sequences. This method eliminates the ligation steps required in known methods for generating knock-out genes, and permits precise targeting of the site in the nucleic acid molecule for insertion of a cassette or deletion of sequences. Further, the method of the invention is readily adapted for use in high throughput screening.

Thus, the invention provides a method for modifying a nucleic acid molecule at a predetermined target site by insertion and/or deletion of nucleic acid sequences in the absence of ligation. The method of the invention may be used to make unmarked deletions by using primers having an overlap region. More desirably, the method of the invention is used in the production of a modified nucleic acid molecule which is a nucleic acid-cassette fusion. Optionally, this nucleic acid-cassette fusion may be a knock-out construct.

A knock-out construct refers to a modified nucleic acid molecule in which the function of a selected gene in the molecule has been disrupted, either by its deletion (either partial of fully) or by the insertion of a cassette which eliminates its function. In certain instances, a knock-out construct may have both a deletion and an inserted cassette.

As used herein, a nucleic acid molecule is composed of nucleotide sequences of RNA or DNA. The RNA or DNA may be double- or single stranded and may be readily selected from the different subtypes of RNA (e.g. mRNA or tRNA) or DNA (e.g., genornic, chromosomal, or cDNA). Optionally, the nucleotides of these molecules may contain modifications, e.g., labels which are known in the art, methylation, "cap", substitution of one or more of the naturally occurring nucleotides with an analog, and internucleotide modifications. A particular advantage of the method of the invention is that it can readily be applied to nucleic acid molecules regardless of whether they are linear or circular, e.g., plasmids. The nucleic acids used in the method of the invention may be obtained from any suitable source, including, for example, viruses, plasmids, yeast, gram positive and gram negative bacterial, eukaryotic cells, and the like. Currently, preferred sources of bacterial nucleic acids include the gram-positive Streptococcus and Staphylococcus and the gram negative *Haemophilus influenzae*. However, selected of the nucleic acid molecules is not a limitation of the present invention.

A target site is a location within a nucleic acid molecule or sequence into which a cassette is to be inserted or from which sequences are to be deleted. Suitably, a target site may be composed of two nucleotides, between which an insertion is to be made, or a group of nucleotides, e.g, from two to ten bases in length which are to be deleted and/or into which the cassette is to be inserted. In certain embodiments (e.g., where deletions are to be made), the target site may be larger than 50 bases. In these embodiments, the target site may range from 50 bp to 5000 bp, 500 bp to 3000 bp, 1000 bp to 2500 bp, or other suitable sizes within these ranges. It is not essential that the target site be a coding sequence. In one embodiment, the target sequence may be selected particularly for use in essentiality testing or expression studies.

As used herein, a "cassette" is a nucleic acid sequence targeted for insertion into the target site of nucleic acid molecule and/or for fusion with two regions of the nucleic acid molecule. Such cassettes may be composed of single or double-stranded sequences, and may be linear or circular. While the size of a cassette useful in the invention is not a limitation, it is generally at least 10 nucleotides in length and as large as about 5000 nucleotides in length. Preferably, the nucleic acid sequence is a DNA sequence which performs some function. For example, the cassette may be readily selected from among known marker genes, including, e.g., antibiotic resistance genes (e.g., erythromycin, tetracylines, and chloramphenicols), reporter genes including those which are colorimetrically detectable, regulatory sequences including promoters, terminators, operators, and the like, and other functional DNA sequences, e.g., sequences encoding therapeutic or antigenic proteins. Alternatively, the cassette may be an oligonucleotide which introduces one or more base pair changes into the nucleic acid molecule to produce a desired effect in the resulting modified nucleic acid molecule. In still another alternative, the cassette may simply be a non-functional DNA sequence which is inserted to interrupt translation and expression of a protein encoded by a sequence located downstream of the target site. The cassettes used in the invention are engineered to contain sequences at the 5' and 3' end which overlap with (i.e., are identical to) sequences of the regions of the nucleic acid molecule flanking the target site. Thus, a cassette of the invention composed of double-stranded DNA would have a first strand with, at its 5' end, nucleotide sequences which overlap with nucleotides of a stand of the upstream region and, at its 3' end, nucleotide sequences which overlap with nucleotides of a strand of the downstream region. The region of overlap in sequences is between about 10 nt to about 50 nt in length, and preferably about 15 nt to about 35 nt, and most preferably about 20 nt in length. The cassettes useful in the invention may be readily obtained by a variety of convention methods, including genetic engineering methods and chemical synthesis.

As used herein the term "upstream region" refers to those sequences of nucleic acid which are located 5' to the target site, with reference to the coding strand of the nucleic acid molecule. However, the upstream region need not be composed of sequences which encode a desired protein, peptide or other gene product. Where the target site is located within an open reading frame (ORF), the upstream region preferably contains sequences flanking the targeted ORF. Suitably, where the modified nucleic acid molecule is to be a knock-out construct, the upstream region contains sufficient homology to mediate homologous recombination between the modified nucleic acid molecule and the non-disrupted gene in a host cell into which the modified nucleic acid molecule is transformed. Generally, a length of about 100 nt to about 1000 nt, and preferably, at least about 500 nt, of homologous sequences is considered sufficient. Preferably, these "homologous sequences" contain exact (i.e., 100%) identity of sequences. However, the "homologous sequences" may contain some degree of nonidentity. Where there is some degree of non-identity, the sequences suitably have at least 95% identity, more preferably 97% identity, and most preferably 98–99% identity. In other embodiments, particularly where homologous recombination is not desired following transformation of a host cell, the size of the upstream region may be readily determined by one of skill in the art. For example, the upstream region may be as small as about 100 bp and as large as 500 kb, or more.

The term "downstream region" refers to those sequences of nucleic acids which are located 3' to the target site, with reference to the coding strand of the nucleic acid molecule. As with the upstream region, the downstream region need not be composed of coding sequences; and, where the target site is located within an ORF, the downstream region preferably contains sequences flanking the targeted ORF. Suitably, the size of the downstream region is determined by the factors described above with respect to the upstream region. However, it will be understood that the sizes of the downstream region and upstream region may be selected independently of one another.

It should be noted that although the discussion refers in many locations to double-stranded DNA for purposes of convenience, it will understand that the method of the invention is useful with single-stranded nucleic acid sequences. Further, it will be recognized that even in situations where the nucleic acid molecule and the insertion cassette are double-stranded, single-stranded DNA may be added to the PCR mixture for use in obtaining the desired amplification product(s).

As known in the art, "homology" or "identity" means the degree of sequence relatedness between two polypeptide or two polynucleotide sequences as determined by the identity of the match between two lengths of such sequences. Both identity and homology can be readily calculated by methods extant in the prior art [See, e.g., COMPUTATIONAL MOLECULAR BIOLOGY, Lesk, A. M., ed., Oxford University Press, New York, (1988); BIOCOMPUTING: INFORMATICS AND GENOME PROJECTS, Smith. D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987). and SEQUENCE ANALYSIS PRIMER, Gribskov, M. and Devereux, J., eds., M Stockton Press, New York, (1991)]. While there exist a number of methods to measure identity and homology between two polynucleotide sequences, the terms "identity", "similarity" and homology are well known to skilled artisans [H. Carillo and D. Lipton, *SIAM J. Applied Math.*, 48:1073 (1988)]. Methods commonly employed to determine identity or homology between two sequences include, but are not limited to, those disclosed in Guide to Huge Computers, Martin J. Bishop, ed., Academic Press, San Diego, 1994, and H. Carillo and D. Lipton, *SIAM J. Applied Math.*, 48:1073 (1988). Preferred methods to determine identity or homology are designed to give the largest match between the two sequences tested. Methods to determine identity and similarity are codified in computer programs. Preferred computer program methods to determine identity and homology between two sequences include, but are not limited to, the algorithm BESTFIT from the GCG program package [J. Devereux et al., *Nucl. Acids Res.*, 12(1):387 (1984)], the related MACVECTOR program (Oxford), and the FASTA (Pearson) programs, which may be used at default settings or modified settings such as determined to be suitable by one of skill in the art.

I. Three Stage PCR

It will be readily recognized by one of skill in the art that the methods of the invention may be readily performed using a high throughput format, i.e., the reactions may be performed on a plate containing a multiplicity of reaction chambers, e.g., 96, 384, or 1536 wells. Such plates are readily available from a variety of sources. However, the reactions may similarly be performed in a variety of other suitable reaction vessels, e.g., tubes. Selection of the reaction vessel is not a limitation of the present invention.

Following selection of the target site within the nucleic acid molecule, primers are obtained for specifically amplifying the upstream and downstream regions flanking the target site. Such primers may be readily generated, e.g., by chemical synthesis or other suitable means, based on the knowledge of the sequences of the nucleic acid molecule, particularly in the area of the target site. Currently, it is preferable for all of the primers described for use in the method of the invention to contain 40–50% G+C content to facilitate the PCR reaction. However, it is possible to vary the G+C content within the range of 35% to about 55% of the primer. In one particularly desirable embodiment, a set of two primers is generated for each of the two regions flanking the target site.

Thus, a forward primer, P1, and a reverse primer, P2, for the region upstream of the target site are obtained from commercial sources or generated using conventional techniques. P1 is about 20 nt to about 30 nt, and more preferably, about 20 nt in length. Optionally, this primer may contain restriction sites for use in molecular cloning after generation of the final fusion product. The P1 primer is complementary to the 5' end of a first strand of the region of the nucleic acid molecule upstream of the target site. Most preferably, the P1 primer targets the extreme 5' end of the first strand. However, it may target sequences very distal (e.g., several nucleotides from the extreme 5' end) or sequences that use some of the actual coding region for homology, provided that a sufficient portion of the target site is deleted or disrupted to inactivate its function. P2 is about 30 nt to about 50 nt, and more preferably, about 40 nt in length. In addition to containing reverse sequences of complementarity for the region upstream of the target site, this primer is designed to contain a tail with reverse complementarity to the 5' end of the cassette. This tail is about 20 nt to 30 nt, and preferably 20 nt in length. Generally, the P2 primer is complementary to the 5' end of a second strand (having reverse complementarity to the first strand) immediately upstream (i.e., at the next nt base) of the target site. (Desirably, where coding sequences are targeted, the first strand may be a sense strand and the second strand may be an anti-sense strand.)

Similarly, a forward primer, P3 and a reverse primer, P4, are obtained for the region downstream of the target site. P3 contains a nt tail which has a region of forward polarity to the 3' end of the cassette (i.e., is complementary) and forward sequences for homology to the sequences downstream of the target site. Suitably, the P3 primer is complementary to the 5' end of a first strand immediately upstream of the target site. The tail of P3 may be about 20 nt to 30 nt, and preferably 20 nt in length. P4 is about 20 nt to about 30 nt, and more preferably, about 20 nt in length. Optionally, this primer may contain restriction sites for use in molecular cloning after generation of the modified nucleic acid molecule which is the final fusion product. P4 amplifies the sequences at the 5' end of the second strand (having reverse complementarity to the first strand) of the downstream region of the nucleic acid molecule. Most preferably, the P4 primer targets the extreme 5' end of the second strand. However, it may target sequences very distal (e.g., several nucleotides from the extreme 5' end) or sequences that use some of the actual coding region for homology, provided that a sufficient portion of the target site is deleted or disrupted to inactivate its function.

In certain situations, it may be desired not only to introduce a cassette into a target site, but also to delete sequences from the nucleic acid molecule in order to do so. In such situations, the target site is a short sequence as defined above rather than a location between two nucleotide bases and the primers are designed to amplify the regions upstream and downstream of the sequences of the target site. Similarly, the cassette is designed to contain sequences overlapping with the nucleotide bases flanking either side of the target sequence. Thus, performance of the method steps described herein will result in a modified nucleic acid molecule containing an upstream region fused to the cassette which is fused to a downstream region, and further containing a deletion of the target sequences of the nucleic acid molecule.

A. Stage 1 Amplification

In one desired embodiment, two separate regions of the nucleic acid molecule flanking the target site are produced using the P1/P2 for the upstream homology and P3/P4 for the downstream homology. This amplification is performed using PCR.

The PCR steps performed in the method of the invention are performed with a thermostable DNA or RNA polymerase and a polymerase having 3'–5' exonuclease activity to remove non-template bases at the 3' and 5' ends. For example, an example of a particularly suitable thermostable DNA polymerase is Taq DNA polymerase. The native enzyme may be purified from *Thermus aquiticus* or genetically engineered from, the enzyme may be synthesized or obtained from a commercial source (e.g., as AMPLITAQ®). Taq is particularly desirable because it carries 5' polymerization-dependent exonuclease activity. Thus, if this polymerase is selected, it is only necessary to include in the reaction mixture a proof-reading polymerase with 3' exonuclease activity. Suitably, high fidelity polymerases are also desirable because they possess 3' and/or 5' exonuclease activity. Examples of high fidelity polymerases include Pfu (has 3' proof-reading activity), Pwu (has 5' proof-reading activity), Vent, Deep Vent, Hot Tub, Tfl, and Thr polymerases. However, other suitable polymerases may be selected and obtained from a variety of commercial sources (e.g., Stratagene). Alternatively, other DNA polymerases may be readily selected and 5' and/or 3' exonucleases added if these functions are not provided by the selected polymerase. Such polymerases and exonucleases may be readily selected by one of skill in the art and obtained from a variety of sources. Reaction conditions are as specified by the enzyme supplier with extension times adjusted for the expected product size. See, also, e.g., Sambrook et al, "Molecular Cloning: A Laboratory Manual", 2$^{nd}$ Ed., Cold Spring Harbor Press, Cold Spring Harbor, N.Y. (1989), ch. 14.2–14.4 for a general discussion of suitable PCR reagents, buffers, and conditions.

The upstream and downstream regions of the nucleic acid molecule may be generated in a single reaction, or in separate reactions, as desired. Desirably, the final products are purified to homogeneity. This purification can be performed using conventional techniques, including spin dialysis performed in microconcentrators or polyacrylamide or agarose gel electrophoresis. See, Sambrook et al, cited above. An example of a suitable system which is commercially available includes Qiagen's affinity matrix purfication systems. However, other commercially available systems may be readily selected.

Suitably, the cassette is also amplified via PCR using a proof-reading polymerase as described above for the upstream and downstream regions. The forward primer, R1, and reverse primer, R2, for the cassette are obtained using conventional techniques such as those described above. These primers are generally about 20 to about 30 nt in length. Optionally, the cassette may be amplified in a reaction which also contains the upstream region and downstream region. Alternatively, the cassette is amplified in separate reactions with the upstream region or the downstream region. In yet another alternative, the cassette is amplified prior to mixture with either the upstream or downstream region. Following amplification, the final product is purified to homogeneity as described herein.

B. Stage 2 Amplification

The product resulting from amplification of the cassette is mixed with an approximately equivalent amount of the product of the amplification of the upstream region or the product of the amplification of the downstream region. For a typical PCR reaction, the amount of each amplification product mixed is about 0.1 μg. However, these amounts may be adjusted, e.g, from as low as 0.05 μg to as high as about 0.5 μg to about 1.0 μg. In these separate PCR reactions using proof-reading polymerases as described above for stage I amplification, the appropriate primers are used. More particularly, for the mixture containing the upstream region and the cassette, primers P1 and R2 are used. The resulting product is a fusion product having the 3' end of a first strand of the upstream region fused to the 5' end of the first strand of the cassette. For the mixture containing the cassette and the downstream region, primers R1 and P4 are used. The resulting fusion product is the 3' end of the first strand of the cassette fused to the 5' end of the first strand of the downstream region. Preferably, the resulting fusion products are purified to homogeneity.

C. Stage 3 Amplification

The purified fusion products generated as described above are then mixed and subjected to PCR in order to generate a modified nucleic acid molecule which contains the cassette in the target site of the selected nucleic acid molecule, flanked by the upstream region and the downstream region. While this PCR may be performed as above, using convention PCR steps with a proof-reading polymerase, it has been found that a modification to these standard techniques provides better yield.

Thus, the third amplification stage involves the following procedure. A mixture containing the products to be amplified, e.g., the two fusion products obtained from stage 2 amplification, is heated in the absence of polymerase or primers. Suitably, this may be performed in a standard buffering solution, e.g., 50 mM KCl, 10 mM Tris.Cl and 1.5 mM MgCl$_2$. The heating step is performed for about 2 to about 8 minutes, preferably about 5 minutes, to a temperature of about 85° C. to about 96° C., and preferably about 94° C. The heated mixture is then taken to a temperature of about 45° C. to 55° C., and most preferably about 50° C., over an extended period of time. Most suitably, the cooling takes place over at least about 20 minutes, and preferably over at least 30 minutes. Thereafter, the mixture is maintained at about the same temperature, e.g., at about 50° C., for at least about 5 minutes. However, this temperature may be maintained for a longer period of time such as an hour, several hours, or overnight, if required for convenience.

Following this incubation at 50° C., a thermostable polymerase is added to the mixture. A suitable RNA or DNA polymerases may be readily selected. See, discussion of polymerases in section relating to stage 1 amplification. The mixture containing the products for amplification and the polymerase (and exonucleases) are heated to about 55° C. to about 75° C. for about 3 to about 20 minutes. Preferably, this heating is performed at about 72° C. for about 5 minutes. The primer P1 for the upstream region and the primer P4 for the downstream region are then added to the mixture which is subjected to a standard 30 cycles of PCR with an extension time appropriate for the expected full-length product.

The resulting full-length product is a modified nucleic acid molecule containing the upstream region fused to the cassette which is fused to the downstream region. Optionally, the product is purified to homogeneity prior to further amplification. Alternatively, the product may be subjected to further amplification via PCR prior to purification. Thus, the method of the invention provides a modified nucleic acid molecule containing the cassette in the target site which is flanked by the upstream and downstream region.

Optionally, the plates or tubes containing the final product, i.e., modified nucleic acid molecule, may be stored in the freezer (e.g., at −80° C.) while awaiting further testing. Where desired, the final product is purified using any of a variety of suitable means, e.g., agarose gel electrophoresis, and, optionally, a sample may be sequenced to confirm the identity of the product.

II. Two-stage PCR

In another embodiment, the method of the invention also permits one to produce a modified nucleic acid molecule, which does not require separate generation of the upstream region/cassette and cassette/downstream region fusion products. In other words, stage 1 and stage 3 amplification are performed as described herein for the three-stage method, but stage 2 amplification is eliminated. As with the three-stage PCR embodiment of the invention, this method may be performed in a multi-well plate, a tube, or in any other suitable reaction vessel.

In such an embodiment, the upstream region, cassette and downstream region may be produced as described in stage 1 above. Briefly, P1/P2 are used for the upstream region of the nucleic acid molecule and P3/P4 for the downstream region of the nucleic acid, using PCR with a high fidelity polymerase possessing 3'–5' exonuclease activity. These regions contain sufficient homology to mediate homologous recombination in a particular host cell. A fusion cassette, R is also amplified with R1 and R2. Reaction conditions are as specified by the enzyme supplier with extension supplier with extension times adjusted for the expected product size. Each final product is purified to homogeneity.

In the final stage of this embodiment of the method of the invention, approximately equivalent amounts of the cassette, upstream region and downstream regions produced are mixed, and amplified as described for stage 3 amplification, using P1 and P4 to PCR amplify the final product. Reaction conditions are as specified by the enzyme supplier with extension times adjusted for the expected product size. The product is purified to homogeneity, and optionally, sequenced to confirm its identity.

III. The Modified Nucleic Acid Molecules

Thus, the three-stage and two-stage PCR methods of the invention may be utilized to construct modified nucleic acid molecules useful for a variety of purposes. These modified nucliec acid molecules may be intermediate products useful for subsequent molecular cloning of a desired construct. For example, a modified nucleic acid molecule of the invention may be engineered to contain restriction sites which permit rapid insertion of a digestion fragment containing a desired portion of the modified nucleic acid molecule and the cassette into a pre-determined location in a desired plasmid or viral vector, or the like. In such an instance, the modified nucleic acid molecules are constructed using primers containing the appropriate restriction sites to facilitate this molecular cloning. Alternatively, the modified nucleic acid molecules generated according to the invention may represent a desired end-product, i.e., for testing or for therapeutic or vaccinal use.

A. Assay Formats

Suitably, the invention provides a method for generating modified nucleic acid molecules which are suitable for constructing gene knockouts for in vitro or iii vivo testing of specific genes, and particularly for testing whether such specific genes are essential for a particular function. It may be desirable in these embodiments for the cassettte inserted to contain a reporter or marker gene, as defined above. However, in other embodiments, the use of a gene encoding a therapeutic protein is desirable and assays are performed to determine the effect of expression of the therapeutic protein on a selected host cell.

In one embodiment, gene knockouts may be tested in vitro using a high throughput assay format. Suitably, the modified nucleic acid molecules containing the disrupted gene are constructed according to the three-stage or two-stage PCR method of the invention and contain a cassette with a marker gene. Thereafter, a suitable host cell which contains a functional gene corresponding to the gene disrupted in the modified nucleic acid molecule of the invention is added to each of the wells. For example, if the modified nucleic acid molecule is a plasmid or linear fragment containing sequences from *Streptococcus pneumoniae* with a functional deletion in a selected gene, one may add *Strep. pneumioniae* cells to wells containing the modified nucleic acid molecules produced according to the present invention. The plates are then incubated under conditions which promote transformation of the cells with the modified nucleic acid molecules. Most preferably, the cells used are "pre-competent" and are grown through the competent phase in the presence of the knock-out constructs. Optionally, the competent phase by be induced by competence stimulating peptide (CSP). Thereafter, the plates are checked for the presence or absence of cell growth. Transformation of the cells is confirmed by detection of the marker. Where the presence of the marker is detectable, the absence of cell growth is an indication that the selected gene functionally deleted from the knockout is essential for cell growth. Positive cell growth indicates that the functionally deleted gene is non-essential for cell growth. A similar assay format may be used to determine the impact of a foreign gene on a selected host cell, where the modified nucleic acid construct of the invention contains a cassette encoding a heterologous gene product. Alternatively, the modified nucleic acid molecules of the invention may be used in vivo assays, many of which are known in the art. Selection of suitable in vitro and in vivo assays are not a limitation of the present invention.

In another embodiment, the method permits the rapid construction of fusion molecules encoding therapeutic or antigenic proteins for expression studies and the like. For example, this may provide a rapid method of generating vaccinal or therapeutic viral vectors, or modified bacterial vaccine candidates. In these embodiments, the cassette may include a transgene under the direction of regulatory sequences which direct its expression in a host cell. Thus, the cassette may be engineered to contain a promoter, enhancer, transcription initiation or termination sequences, efficient RNA processing signals such as splicing and polyadenylation signals (which may contain splice donor and acceptor sites), sequences that stabilize cytoplasmic mRNA, sequences that enhance translation efficiency (i.e., Kozak consensus sequence), sequences that enhance protein stability and, when desired, sequences that enchance protein secretion, as well as other regulatory and expression control sequences. In one embodiment, the method of the invention may be used to place a chromosomal gene copy under the control of a regulatable promoter, or to place a foreign gene controlled by a regulatable promoter in a non-essential site on the chromosome. Thus, promoters may be constitutitive or inducible or regulatable. Selection of suitable promoters and other vector elements are conventional and many such regulatory and expression control sequences are available [see, e.g., Sambrook et al, and references cited therein at, for example, pages 3.18–3.26 and 16.17–16.27 and Ausubel et al., *Current Protocols in Molecular Biology*, John Wiley & Sons, New York, 1989].

B. Pharmaceutical Compositions

The modified nucleic acid molecules of the invention may be useful for in vitro, ex vivo, or in vivo delivery of a transgene to a selected host cell. Alternatively, the modified nucleic acid molecules of the invention may be useful in pharmaceutical compositions for ex vivo or in vivo delivery of a transgene for therapeutical or vaccinal purposes. Such pharmaceutical compositions contain the modified nucleic acid molecule produced according to the method of the invention formulated with a pharmaceutically acceptable carrier, such water, a saline solution, a vegetable oil, or mixtures thereof. Other suitable carriers may be readily selected by one of skill in the art and are not a limitation of the present invention. Still other components customarily employed in the preparation of pharmaceutical compositions may be advantageously included, including, adjuvants, preserving agents, coloring agents, and the like.

Suitably, the molecules of the invention are combined with one or more pharmaceutically acceptable carriers, for examples, solvents, diluents and the like, and are administered in the form of sterile injectable solutions or suspensions containing the molecules in an isotonic medium. Generally, the modified nucleic acid molecules of the invention are delivered in an amount of about 0.01 μg to 100 mg per kg body weight. The molecules may be suspended in a carrier, as identified above, and delivered in doses of from about 1 mL to about 30 mL by any suitable route, including, without limitation, intravenous, intramuscular, subcutaneous, and oral. The method of administration is not limited to the delivery routes specified herein. It is within the skill of one in the art to determine the appropriate dosage regimen, taking into consideration such factors as the condition to be treated, the age, weight, sex and condition of the patient, and the like.

The following examples demonstrate product of several modified nucleic acid molecules using the methods of the invention. These examples are illustrative only and are not a limitation of the present invention.

EXAMPLE 1

Two-piece PCR Method Used to Make an Erythromycin-resistant Knockout Cassette which when Transformed Into *Streptococcus Pneumoniae* Demonstrated fabH Essentially

*S. pneumoniae* gene identified as fabH, primers to the gene sequence were designed follows. The bold underlined regions are complementary to R1 and R2 which in this experiment are designed to amplify up the ermAM erythromycin resistance gene; and the non-underlined regions are homologous to DNA sequences in or flanking fabH:

P1 [SEQ ID NO: 1] 5'TAAGGGGCTACATTGAC-CGAGTTC 3'
P2 [SEQ ID NO: 2] 5' CCGCCATTCTTTGCTGTTTCGTTCCAGCTTGCCA TCAGTTTCT 3'
P3 [SEQ ID NO: 3] 5' GGAAAGTTACACGTTACTAAAGGCTGGGGCACGCT CATTCTTACA 3'
P4 [SEQ ID NO: 4] 5'TTTTCATAGTGCCTCCAACCTT3'
P5 [SEQ ID NO: 5] 5'CTTATTTTTACCCATGCCCTTGT3'
P6 [SEQ ID NO: 6] 5'CAGGCCATCCCTCCTrG-GAAAATA 3'
R1 [SEQ ID NO: 7] 5'CGAAACAGCAAAGAATGGCGG 3'
R2 [SEQ ID NO: 8] 5'CCTTTAGTAACGTGTAACTTTC3'

The two-piece PCR reaction was performed using *S. pneumoniae* isolated chromosomal DNA as template. In separate PCR reactions, P1/P2 were used to produce the upstream region and P3/P4 were used to produce the downstream region using PCR with Taq polymerase (AMPLITAQ®) and Pfu proof-reading polymerase. Reaction conditions were as specified by the enyzme supplier with extension times adjusted for the expected product size. The cassette was produced using a similar PCR reaction. Each final product was purified to homogeniety on an agarose gel column.

P1/P2 413 bp
P3/P4 437 bp
R1/R2 941 bp

The Stage II purified modified nucliec acid molecule consisting of a fabH knockout construct was sequenced to confirm its identity and used to transform *S. pneumoniae* R6 competent cells was transformed using standard techniques. Briefly, the DNA was incubated with pre-competent cells, which are allowed to grow to permit phenotypic expression of the marker, and transformants identified folowing growth under selective conditions. No colonies were obtained after 3 attempts, indicating that the fabH gene is essential in *S. pneumoniae*.

EXAMPLE 2

Three-piece PCR Method Used to Make an Erythromycin-resistant Knockout Cassette which when Transformed Into Streptococcus Pneumoniae Demonstrated fabH Essentiality In order to knockout the *S. pneumoniae* gene identified as fabH, primers to the gene sequence were designed as follows. The bold underlined regions are complementary to R1 and R2 which in this experiment are designed to amplify up the ermAM erythromycin fabH:

P1 [SEQ ID NO: 10] 5'TAAGGGGCTACATTGAC-CAGTTC 3'
P2 [SEQ ID NO: 11] 5' CCGCCATTCTTTGCTGTTTCGTTCCAGCTTTTGCC ATCAGTTC 3'
P3 [SEQ ID NO: 12]5' GGAAAGTTACACGTTACTAAAGGCTGGGGCACGC TCATTCTTAC3'
P4 [SEQ ID NO: 13] 5'TTTTCATAGTGCCTCCAAC-CTT3'
P5 [SEQ ID NO: 14] 5'CTTATTTTTACCCATGCCCT-TGTA 3'
P6 [SEQ ID NO: 15] 5'CAGGCCATCCCTCCTTG-GAAAATA 3'
R1 [SEQ ID NO: 16] 5'CGAAACAGCAAAGAATGGCGG 3'
R2[SEQ ID NO: 17]5'CCTTTAGTAACGTGTAACTTTCC 3'

The three-piece PCR reaction was set up using *S. pneumoniae* isolated chromosomal DNA as template. The Stage I reactions were performed as described in Example 1, using the primers of this example. The product sizes were determined by azarose gel electrophoresis:

P1/P2 413 bp

P3/P4 437 bp
R1/R2 941 bp

In Stage II, two separate PCRs were performed using Taq polymerase as in the first stage reaction. In a first PCR, 0.1 μg of each of the products from PCR of the cassette and the upstream region of *S. pneumoniae* were mixed and in a second PCR reaction, 0.1 μg of each of the products from PCR of the cassette and the downstream region of *S. pneumoniae* were mixed. For the upstream reaction, primers P1 and R2 were used. For the downstream reaction, primers R1 and P4 were used. The two resulting fusion products, i.e., upstream region/cassette and cassette/downstream region, were purified to homogeneity prior to Stage III.

Stage III was performed by mixing 0.5 μg of each the upstream region/cassette and cassette/downstream region in a standard Taq polymerase PCR without polymerase or primers. The reaction was held for 5 minutes at 94° C., and then taken to 50° C. over a ramp period of 30 minutes. The reactions was then held at 50° C. for 5 minutes. During this time, 2.5 U of Taq polymerase was added, and the reaction was taken to 72° C. for an extension time of 5 minutes. After this period, P1 and P4 are added, and the reaction was subjected to a standard 30 cycle PCR.

The Stage III purified fabH knockout cassette was sequenced to confirm its identity and used to transform *S. pneumoniae* competent cells. No colonies were obtained after 3 attempts, indicating that the fabH gene is essential in *S. pneumoniae*.

Similar methods may be used to assay the function of non-essential genes. Where the gene is non-essential, mutant colonies will be obtained. Southern blot analysis and diagnostic PCR reactions can be used to assay the band sizes following agarose gel electrophoresis.

EXAMPLE 3

Three-stage PCR Method Used to Make a Knockout Cassette which was Cloned into a *Staphylococcus aureus* Plasmid for Essentiality Studies In order to knockout the *S. aureus* gene identified as era, primers to the gene sequence were designed as follows. The bold underlined regions are complementary to R1 and R2 which in this experiment are designed to amplify the ermC erythromycin resistance gene; and the non-underlined regions are homologous to DNA sequences in or flanking era. The lower case bases represent thermal clamps (cgc) and recognition sites (ggatcc) for the restriction enzyme BamHI used for cloning purposes:

P1 [SEQ ID NO: 18] 5'cgcggatccTGTTGTAGATTTAGT-GACCG 3'

P2 [SEQ ID NO: 19] 5' CGGGATACAAAGACATAATCTTCCCTACATTTGG TCTACC 3'

P3 [SEQ ID NO: 20] 5' GTAAGTTAAGGGATGCATAATGGTTATGTTGAAG ACCAAG3'

P4 [SEQ ID NO: 21] 5'cgcggatccTCAGCTTGTGTGTCAT-TACC 3'

P6 [SEQ ID NO: 22] 5'ATCTTTAGAAGCCTCTTGCC 3'

R1 [SEQ ID NO: 23] 5'GATTATGTCTTTGTATCCCG 3'

R2 [SEQ ID NO: 24] 5'TTATGCATCCCTTAACTTAC 3'

The three-piece PCR reaction was set up as described in section B above using *S. aureus* WCUH29$_c$ isolated chromosomal DNA as template. The Stage I reactions produced products of the predicted sizes as determined by agarose gel electrophoresis:

P1/P2 615 bp
P3/P4 530 bp
R1/R2 1234 bp

The Stage III purified knockout cassette was cloned into pBluescript-tetA at the BamHi site to produce pEra. pEra was introduced into *S. aureus* RN4220 by electroporation. Colonies were obtained that were dual Em$^R$ and Tc$^R$, and represented plasmid insertion cointegrants at the era locus. Diagnostic PCR products were obtained with:

RIP6 1825 bp

Indicating that the plasmid had integrated into the chromosome using the right flank (P3/P4) of homology with era.

A φ11 bacteriophage lysate was prepared on the cointegrant strain, and the resulting transducing phage were used to infect WCUH29$_c$. Clones were selected that were Em$^R$ and Tc$^S$. These clones represented recombination events involving repeated sequences of the right flanking region generated during cointegrant formation, such that plasmid sequences were excised leaving behind an allelic exchange mutation of era. The predicted structure of the allelic exchange was indicated by diagnostic PCR with:

P1/P4 2379 bp

Since the ermC cassette introduced a new NsiI site into the era locus, the structure could be confirmed by Southern hybridization.

For genes that are essential for in vitro viability, Em$^R$ and Tc$^S$ clones would not be recovered.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for inserting a cassette into a DNA molecule to produce a DNA sequence fusion cassette without requiring ligation, said method comprising the steps of:

(a) providing a selected DNA molecule comprising a first region of DNA sequences upstream of a site targeted for disruption and a second region of DNA sequences downstream of the site targeted for disruption, wherein said first region of DNA sequences upstream of a site targeted for disruption further comprises a first strand having a first and a second end, and said second region of DNA sequences downstream of the site targeted for disruption further comprises a first strand having a first and a second end;

(b) providing a cassette comprising a first strand of DNA, wherein the first strand of said cassette comprises at its 5' end DNA sequences which overlap with sequences at the second end of the first region of DNA sequences upstream of a site targeted for disruption, and at its 3' end DNA sequences which overlap with sequences of the first end of the second region of DNA sequences downstream of the site targeted for disruption;

(c) amplifying the first region of DNA sequences upstream of a site targeted for disruption using primers for said first region and amplifying the second region of DNA sequences downstream of the site targeted for disruption using primers for said second region thereby producing amplified first and second regions;

(d) mixing the cassette with the amplified first and second regions thereby producing a mixture;

(e) amplifying the mixture of (d) using polymerase chain reaction, thereby producing without ligation a DNA sequence fusion cassette comprising the first region of DNA sequences and second region of DNA sequences flanking the cassette, wherein said amplifying further comprises the steps of:

(i) heating the mixture of (d) for about 5 minutes in the absence of polymerase or primers at about 94° C.;

(ii) cooling the mixture of (i) to 50° C. over about 30 minutes;

(iii) maintaining the mixture of (ii) at about 50° C. for about 5 minutes;

(iv) adding a thermostable polymerase to the mixture of (iii);

(v) adding a proof-reading polymerase with 3' exonuclease activity to the mixture of (iv);

(vi) heating the mixture of (v) to about 72° C. for about 5 minutes; and (vii) adding to the mixture of (vi) primers comprising a 5' forward primer P1 complementary to said first region and a 3' reverse primer P4 complementary to said second region.

2. A method for inserting a cassette into a DNA molecule to produce a DNA sequence fusion cassette without requiring ligation, said method comprising the steps of:

(a) providing a first region of DNA sequences and a second region of DNA sequences, said first and second regions each comprising a first strand having a first and second end;

(b) mixing with the first and second regions a cassette comprising a first strand of DNA, wherein the first strand of said cassette comprises at its 5' end DNA sequences which overlap with sequences at the second end of the first region, and at its 3' end DNA sequences which overlap with sequences of the first end of the second region thereby producing a mixture;

(c) heating the mixture of (b) for about 5 minutes in the absence of polymerase or primers at about 94° C.;

(d) cooling the mixture of (c) to 50° C. over about 30 minutes;

(e) maintaining the mixture of (d) at about 50° C. for about 5 minutes;

(f) adding a thermostable polymerase to the mixture of (e);

(g) adding a proof-reading polymerase with 3' exonuclease activity to the mixture of (f);

(h) heating the mixture of (g) to about 72° C. for about 5 minutes;

(i) adding to the mixture of (h) primers comprising a 5' forward primer P1 complementary to the first region and a 3' reverse primer P4 complementary to the second region, and (j) amplifying the mixture of (i) using polymerase chain reaction, thereby producing without ligation a DNA sequence fusion cassette comprising the first region of DNA sequence and second region of DNA sequences flanking the cassette.

* * * * *

SEQUENCE LISTING

<160> NUMBER OF SEQ ID NOS: 24

<210> SEQ ID NO 1
<211> LENGTH: 24
<212> TYPE: DNA
<213> ORGANISM: Streptococcus pneumoniae

<400> SEQUENCE: 1 taagggcta cattgaccga gttc    24

```
<210> SEQ ID NO 2
<211> LENGTH: 45
<212> TYPE: DNA
<213> ORGANISM: Streptococcus pneumoniae

<400> SEQUENCE: 2
ccgccattct tgctgtttc gttccagctt ttgccatcag tttct            45

<210> SEQ ID NO 3
<211> LENGTH: 45
<212> TYPE: DNA
<213> ORGANISM: Streptococcus pneumoniae

<400> SEQUENCE: 3
ggaaagttac acgttactaa aggctggggc acgctcattc ttaca            45

<210> SEQ ID NO 4
<211> LENGTH: 22
<212> TYPE: DNA
<213> ORGANISM: Streptococcus pneumoniae

<400> SEQUENCE: 4
ttttcatagt gcctccaacc tt                                     22

<210> SEQ ID NO 5
<211> LENGTH: 23
<212> TYPE: DNA
<213> ORGANISM: Streptococcus pneumoniae

<400> SEQUENCE: 5 cttatttta cccatgccct tgt                                     23

<210> SEQ ID NO 6
<211> LENGTH: 24
<212> TYPE: DNA
<213> ORGANISM: Streptococcus pneumoniae

<400> SEQUENCE: 6
caggccatcc ctccttggaa aata                                   24

<210> SEQ ID NO 7
<211> LENGTH: 21
<212> TYPE: DNA
<213> ORGANISM: Streptococcus pneumoniae

<400> SEQUENCE: 7
cgaaacagca aagaatggcg g                                      21

<210> SEQ ID NO 8
<211> LENGTH: 22
<212> TYPE: DNA
<213> ORGANISM: Streptococcus pneumoniae

<400> SEQUENCE: 8
cctttagtaa cgtgtaactt tc                                     22

<210> SEQ ID NO 9
<211> LENGTH: 23
<212> TYPE: DNA
<213> ORGANISM: Streptococcus pneumoniae

<400> SEQUENCE: 9
taaggggcta cattgaccag ttc                                    23
```

```
<210> SEQ ID NO 10
<211> LENGTH: 44
<212> TYPE: DNA
<213> ORGANISM: Streptococcus pneumoniae

<400> SEQUENCE: 10
ccgccattct tgctgtttc gttccagctt tgccatcag tttc           44

<210> SEQ ID NO 11
<211> LENGTH: 44
<212> TYPE: DNA
<213> ORGANISM: Streptococcus pneumoniae

<400> SEQUENCE: 11
ggaaagttac acgttactaa aggctggggc acgctcattc ttac           44

<210> SEQ ID NO 12
<211> LENGTH: 22
<212> TYPE: DNA
<213> ORGANISM: Streptococcus pneumoniae

<400> SEQUENCE: 12
ttttcatagt gcctccaacc tt                                   22

<210> SEQ ID NO 13
<211> LENGTH: 24
<212> TYPE: DNA
<213> ORGANISM: Streptococcus pneumoniae

<400> SEQUENCE: 13 cttatttta cccatgccct tgta                                  24

<210> SEQ ID NO 14
<211> LENGTH: 24
<212> TYPE: DNA
<213> ORGANISM: Streptococcus pneumoniae

<400> SEQUENCE: 14
caggccatcc ctccttggaa aata                                 24

<210> SEQ ID NO 15
<211> LENGTH: 21
<212> TYPE: DNA
<213> ORGANISM: Streptococcus pneumoniae

<400> SEQUENCE: 15
cgaaacagca aagaatggcg g                                    21

<210> SEQ ID NO 16
<211> LENGTH: 23
<212> TYPE: DNA
<213> ORGANISM: Streptococcus pneumoniae

<400> SEQUENCE: 16
cctttagtaa cgtgtaactt tcc                                  23

<210> SEQ ID NO 17
<211> LENGTH: 29
<212> TYPE: DNA
<213> ORGANISM: Streptococcus aureus

<400> SEQUENCE: 17
```

-continued

```
cgcggatcct gttgtagatt tagtgaccg                                    29

<210> SEQ ID NO 18
<211> LENGTH: 40
<212> TYPE: DNA
<213> ORGANISM: Streptococcus aureus

<400> SEQUENCE: 18
cgggatacaa agacataatc ttccctacat ttggtctacc                        40

<210> SEQ ID NO 19
<211> LENGTH: 40
<212> TYPE: DNA
<213> ORGANISM: Streptococcus aureus

<400> SEQUENCE: 19
gtaagttaag ggatgcataa tggttatgtt gaagaccaag                        40

<210> SEQ ID NO 20
<211> LENGTH: 29
<212> TYPE: DNA
<213> ORGANISM: Streptococcus aureus

<400> SEQUENCE: 20
cgcggatcct cagcttgtgt gtcattacc                                    29

<210> SEQ ID NO 21
<211> LENGTH: 20
<212> TYPE: DNA
<213> ORGANISM: Streptococcus aureus

<400> SEQUENCE: 21
atctttagaa gcctcttgcc                                              20

<210> SEQ ID NO 22
<211> LENGTH: 20
<212> TYPE: DNA
<213> ORGANISM: Streptococcus aureus

<400> SEQUENCE: 22
atctttagaa gcctcttgcc                                              20

<210> SEQ ID NO 23
<211> LENGTH: 20
<212> TYPE: DNA
<213> ORGANISM: Streptococcus aureus

<400> SEQUENCE: 23
gattatgtct ttgtatcccg                                              20

<210> SEQ ID NO 24
<211> LENGTH: 20
<212> TYPE: DNA
<213> ORGANISM: Streptococcus aureus

<400> SEQUENCE: 24
ttatgcatcc cttaacttac                                              20
```